(12) United States Patent
Karadogan (10) Patent No.: US 11,185,419 B2
(45) Date of Patent: Nov. 30, 2021

(54) ARTIFICIAL INTERVERTEBRAL DISCS

(71) Applicant: Central Michigan University, Mount Pleasant, MI (US)

(72) Inventor: Ernur Karadogan, Mount Pleasant, MI (US)

(73) Assignee: CENTRAL MICHIGAN UNIVERSITY, Mt. Pleasant, MI (US)

( * ) Notice: Subject to any disclaimer, the term of this patent is extended or adjusted under 35 U.S.C. 154(b) by 0 days.

(21) Appl. No.: 16/777,530

(22) Filed: Jan. 30, 2020

(65) Prior Publication Data

US 2020/0246155 A1 Aug. 6, 2020

Related U.S. Application Data

(60) Provisional application No. 62/800,116, filed on Feb. 1, 2019.

(51) Int. Cl.
*A61F 2/44* (2006.01)
*A61F 2/30* (2006.01)

(52) U.S. Cl.
CPC .... *A61F 2/441* (2013.01); *A61F 2002/30092* (2013.01); *A61F 2002/444* (2013.01); *A61F 2002/4435* (2013.01); *A61F 2002/4495* (2013.01); *A61F 2310/00023* (2013.01); *A61F 2310/00029* (2013.01); *A61F 2310/00077* (2013.01)

(58) Field of Classification Search
CPC ............... A61F 2/441; A61F 2002/444
See application file for complete search history.

(56) References Cited

U.S. PATENT DOCUMENTS

| | | | | |
|---|---|---|---|---|
| 3,867,728 | A * | 2/1975 | Stubstad | A61F 2/441 623/17.16 |
| 4,911,718 | A * | 3/1990 | Lee | A61F 2/442 623/17.15 |
| 6,712,853 | B2 | 3/2004 | Kuslich | |
| 6,733,531 | B1 | 5/2004 | Trieu | |
| 6,746,485 | B1 * | 6/2004 | Zucherman | A61F 2/441 623/17.16 |
| 7,799,078 | B2 | 9/2010 | Embry et al. | |
| 8,986,388 | B2 | 3/2015 | Siegal et al. | |
| 9,186,260 | B2 | 11/2015 | Honma et al. | |

(Continued)

FOREIGN PATENT DOCUMENTS

CN 2892011 Y 4/2007

OTHER PUBLICATIONS

Ayturk, U. M., Garcia, J. J., & Puttlitz, C. M. (2010). The micromechanical role of the annulus fibrosus components under physiological loading of the lumbar spine. Journal of biomechanical engineering, 132(6), 061007.

(Continued)

*Primary Examiner* — Nicholas W Woodall
(74) *Attorney, Agent, or Firm* — Michael Best & Friedrich LLP (57) ABSTRACT

Artificial intervertebral discs include an annulus fibrosus portion and a nucleus pulposus portion. Annulus fibrosus portions disclosed and contemplated herein include a plurality of layers. Fibers within the layers are arranged to provide a crisscross pattern between adjacent layers. Nucleus pulposus portions disclosed and contemplated herein can include a flexible, sealed enclosure.

19 Claims, 6 Drawing Sheets

(56) References Cited

U.S. PATENT DOCUMENTS

| | | |
|---|---|---|
| 10,064,736 B2 | 9/2018 | Khandaker et al. |
| 2002/0123750 A1* | 9/2002 | Eisermann ............... A61F 2/441 606/285 |
| 2005/0043733 A1 | 2/2005 | Eisermann et al. |
| 2005/0119752 A1 | 6/2005 | Williams et al. |
| 2006/0064170 A1 | 3/2006 | Smith et al. |
| 2008/0065218 A1 | 3/2008 | O'Neil |
| 2008/0177392 A1 | 7/2008 | Williams et al. |
| 2009/0222098 A1* | 9/2009 | Trieu ....................... A61L 27/50 623/17.16 |
| 2010/0114320 A1 | 5/2010 | Lange et al. |
| 2011/0270399 A1 | 11/2011 | Yurek et al. |

OTHER PUBLICATIONS

Hanlon, A. D., Cook, D. J., Yeager, M. S., & Cheng, B. C. (2014). Quantitative Analysis of the Nonlinear Displacement-Load Behavior of the Lumbar Spine. Journal of Biomechanical Engineering, 136(8), 081009.

Jamison IV, D. (2013). Mechanical Characterization of the Human Lumbar Intervertebral Disc Subjected to Impact Loading Conditions. Drexel University, 118 pages.

Jamison, D., Cannella, M., Pierce, E. C., & Marcolongo, M. S. (2013). A comparison of the human lumbar intervertebral disc mechanical response to normal and impact loading conditions. Journal of biomechanical engineering, 135(9), 091009.

Luxmoore, B. J. (2013). Computational simulation of the intervertebral disc. University of Leeds, 230 pages.

Shahraki, N. M. (2014). Finite element modeling and damage evaluation of annulus fibrosus, 106 pages.

Shirazi-Adl, S. A., Shrivastava, S. C., & Ahmed, A. M. (1984). Stress analysis of the lumbar disc-body unit in compression. A three-dimensional nonlinear finite element study. Spine, 9(2), 120-134.

Strange, D. G., Fisher, S. T., Boughton, P. C., Kishen, T. J., & Diwan, A. D. (2010). Restoration of compressive loading properties of lumbar discs with a nucleus implant—a finite element analysis study. The Spine Journal, 10(7), 602-609.

Vignollet, J. (2012). Computational strategies toward the modelling of the intervertebral disc (Doctoral dissertation, University of Glasgow) 155 pages.

White, A. A., & Panjabi, M. M. (1990). Clinical biomechanics of the spine (vol. 2, pp. 108-112). Philadelphia: Lippincott.

* cited by examiner

ARTIFICIAL INTERVERTEBRAL DISCS

CROSS-REFERENCE TO RELATED APPLICATIONS

The present application is related to and claims the priority benefit of U.S. Provisional Patent Application No. 62/800,116, filed Feb. 1, 2019, the entire contents of which are incorporated herein by reference.

FIELD OF DISCLOSURE

The present disclosure relates to artificial intervertebral discs. More particularly, the present disclosure relates to artificial intervertebral discs including a nucleus pulposus portion and an annulus fibrosus portion comprising multiple layers.

INTRODUCTION

Intervertebral discs are disposed between vertebrae in a spinal column. Broadly characterized, intervertebral discs provide separation between vertebrae, which can be beneficial in providing shock absorption. Intervertebral discs can also protect nerves in the spinal column.

Human intervertebral discs have an annulus fibrosus (AF) portion and a nucleus pulposus (NP) portion. The AF portion includes several layers, where each layer can include a plurality of fibers. Excessive axial torsion (along with compression and bending) may cause tears in the AF portion and eventually result in disc herniation. In disc herniation, the NP portion may leak through the AF portion. A herniated disc may cause severe pain or even paralysis by pinching on the spinal cord. Artificial intervertebral discs can be used to replace human intervertebral discs.

SUMMARY

Artificial intervertebral discs disclosed and contemplated herein include an annulus fibrosus portion and a nucleus pulposus portion. Annulus fibrosus portions disclosed and contemplated herein include a plurality of layers. Fibers within the layers are arranged to provide a crisscross pattern between adjacent layers. Nucleus pulposus portions disclosed and contemplated herein can include a flexible, sealed enclosure.

In one aspect, an intervertebral disc is disclosed. The intervertebral disc includes a nucleus pulposus portion including a flexible sealed enclosure, the flexible sealed enclosure including filling material therein. The intervertebral disc also includes an annulus fibrosus portion that includes a plurality of layers arranged annularly about the nucleus pulposus portion. Each of the plurality of layers includes biocompatible fibers. A first fiber layer has an orientation that is different from fibers in a second fiber layer, where the second fiber layer is adjacent to the first fiber layer.

Other aspects of the disclosure will become apparent by consideration of the detailed description and accompanying drawings. There is no specific requirement that a material, technique or method include all of the details characterized herein, in order to obtain some benefit according to the present disclosure. Thus, the specific examples characterized are meant to be exemplary applications of the techniques described, and alternatives are possible.

DETAILED DESCRIPTION

Artificial intervertebral discs described and contemplated herein are particularly well suited for use in disc replacement procedures. In some instances, artificial disc replacement procedures are used to treat people experiencing back pain. Although typical use of artificial intervertebral discs involves replacing discs near the lower spine area, artificial intervertebral discs disclosed and contemplated herein can be used to replace discs at various parts of a spinal column.

Artificial intervertebral discs described and contemplated herein include both a nucleus pulposus portion and an annulus fibrosus portion. The annulus fibrosus portion of artificial intervertebral discs disclosed and contemplated herein include multiple layers, where each layer includes fibers. These fibers can provide improved biomechanical response of the artificial intervertebral discs. In the following sections, aspects of example artificial intervertebral discs are described. Example embodiments of artificial intervertebral discs are also described.

Figure 1:
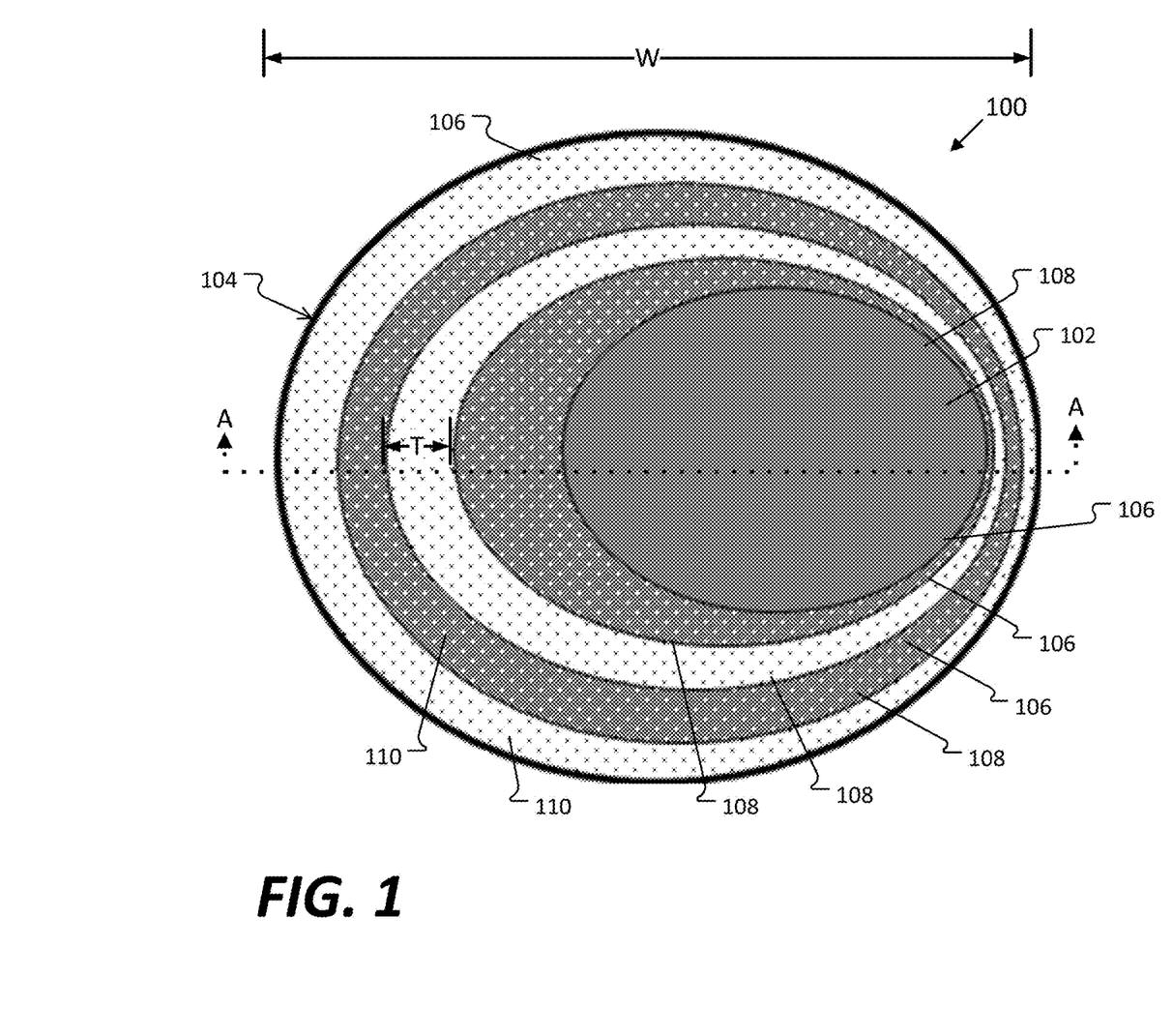
FIG. 1 is a schematic, top view of an example artificial intervertebral disc.
Figure 2:
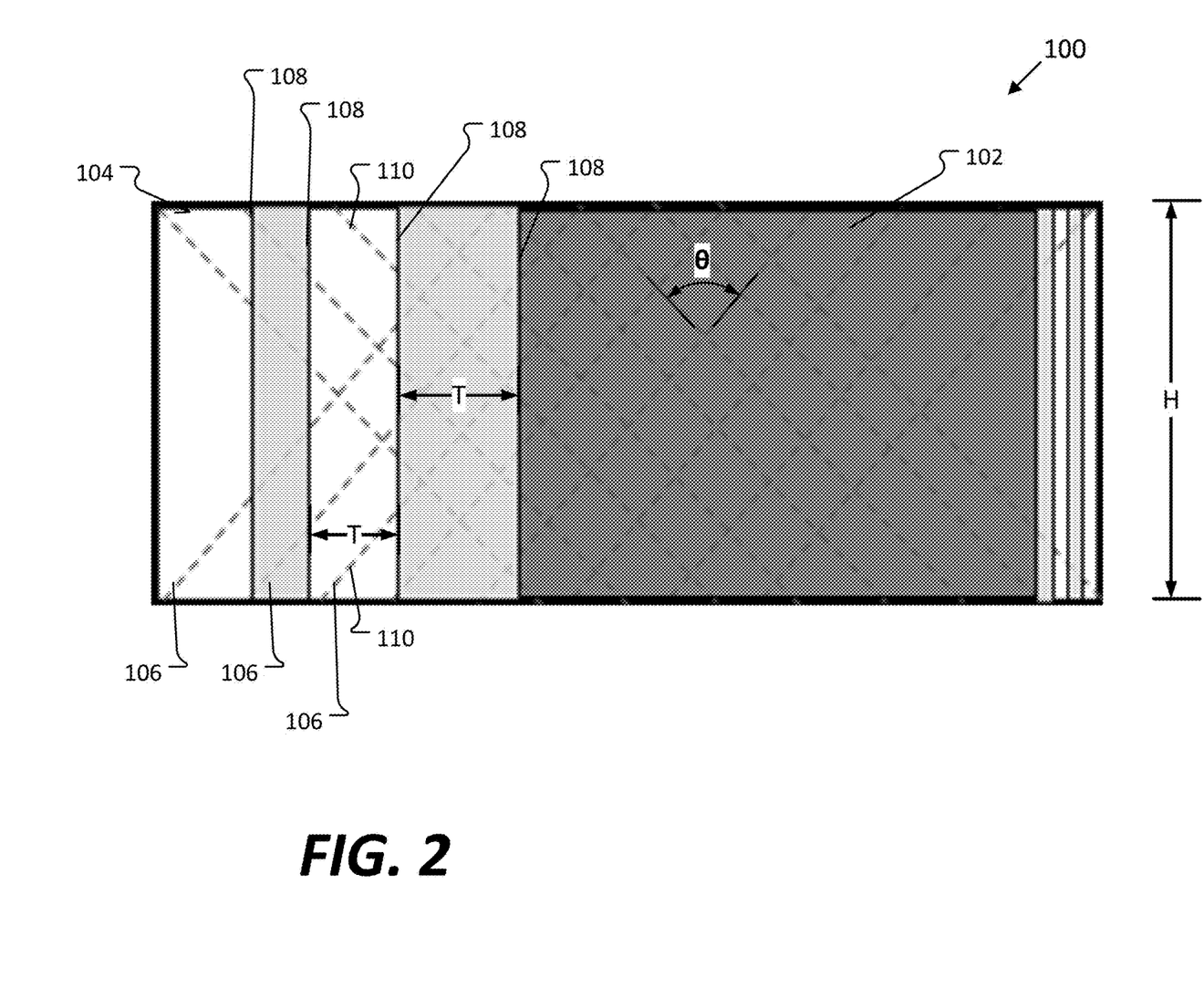
FIG. 2 is a side sectional view of the artificial intervertebral disc, taken along section line A-A in FIG. 1.

With reference to FIGS. 1 and 2, a width dimension of an artificial intervertebral disc 100 is indicated with "W" and a height dimension with "H." For convenience of reference, this disclosure uses the term "horizontal" to mean generally along the width W of a disc and the term "vertical" to mean generally along the height "H" of a disc.

I. Example Artificial Intervertebral Discs

Example artificial intervertebral discs described and contemplated herein can be characterized by nucleus pulposus portion, annulus fibrosus portion, plates, and materials of construction.

A. Example Nucleus Pulposus Portions

Artificial intervertebral discs disclosed and contemplated herein include a nucleus pulposus portion. Broadly characterized, the nucleus pulposus portion is a flexible, sealed enclosure. A filling material is disposed within the flexible, sealed enclosure. In some implementations, the filling material is an incompressible fluid. Example incompressible fluids usable in the flexible, sealed enclosure include gels and high viscosity liquids.

Various gels can be used as the incompressible fluid. Example gels include, but are not limited to, hydrogel and low molecular weight poly(dimethylsiloxane). In some embodiments, silicone rubber can be used as the filling material.

In various implementations, example nucleus pulposus portions occupy 30% to 60% of a horizontal cross-sectional area of the artificial intervertebral disc. In some instances, nucleus pulposus portions occupy 30% to 50%; 40% to 60%; 40% to 50%; 30% to 40%; or 50% to 60% of the horizontal cross-sectional area of the artificial intervertebral disc.

Nucleus pulposus portions can be positioned at various relative positions within the example artificial intervertebral discs. For example, nucleus pulposus portions can be positioned horizontally off-center in the artificial intervertebral disc. An example method of determining whether a nucleus pulposus portion is off center is to compare relative positions of a centroid of the nucleus pulpous portion and a centroid of the artificial intervertebral disc. In some instances, nucleus pulposus portions can be horizontally centered in the artificial intervertebral disc.

B. Example Annulus Fibrosus Portions

Artificial intervertebral discs disclosed and contemplated herein include an annulus fibrosus portion. Example annulus fibrosus portions include a plurality of layers arranged annularly about the nucleus pulposus portion. The layers extend vertically through the height H of the disc and are identified by their horizontal spacing from the NP. For example, a "first layer" is a layer immediately surrounding the NP, a "second layer" is a layer immediately surrounding the first layer, and a "third layer" is a layer immediately surrounding the second layer, etc. The second layer is horizontally spaced further from the NP than the first layer, but not as far as the third layer.

Figure 3A:
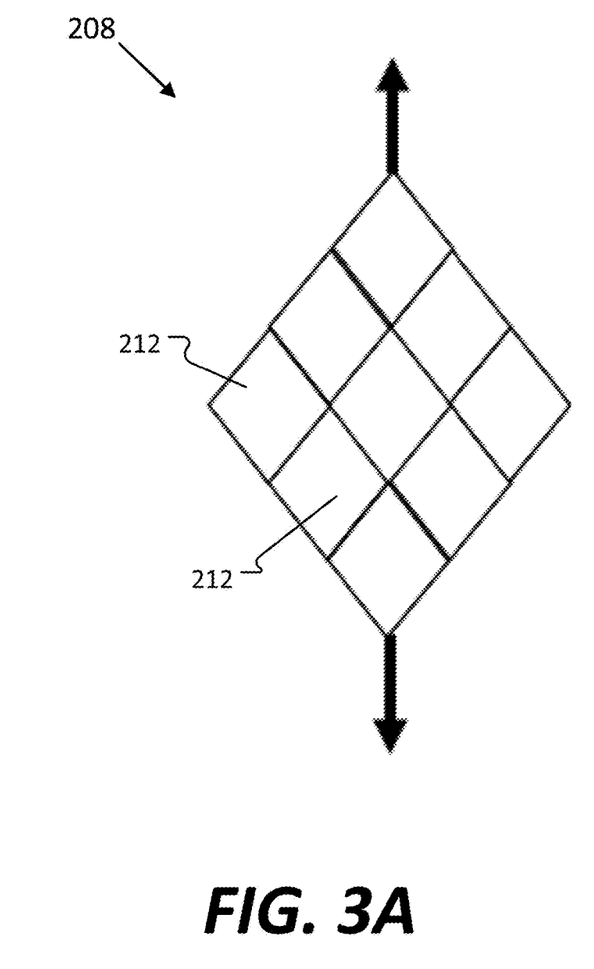
FIG. 3A is a side sectional view of an example shape memory alloy mesh usable in the artificial intervertebral disc shown in FIG. 1.
Figure 3B:
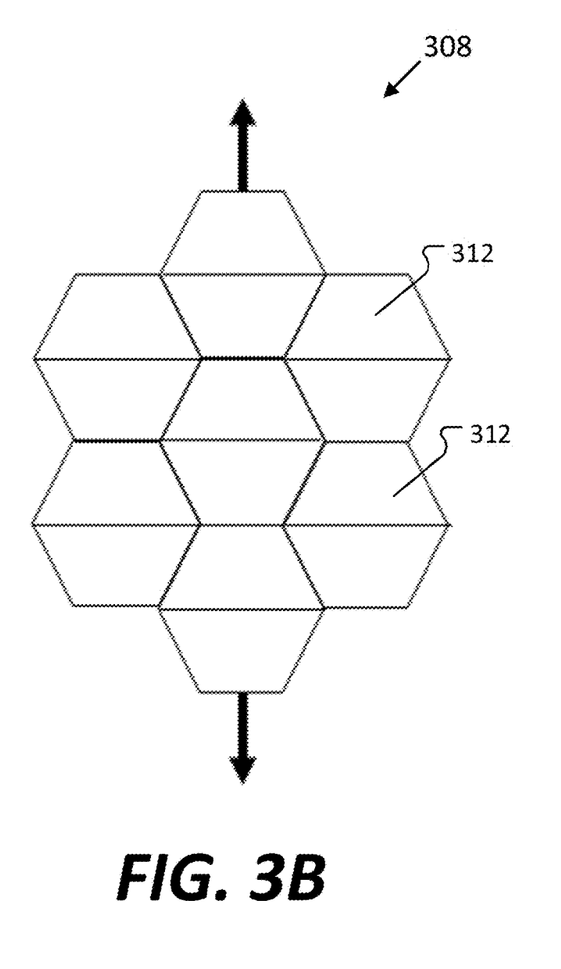
FIG. 3B is a side sectional view of another example shape memory alloy mesh usable in the artificial intervertebral disc shown in FIG. 1.

The plurality of layers in example annulus fibrosus portions include biocompatible fibers. Typically, each biocompatible fiber includes one or more wires. Wires in a given fiber can be arranged in various configurations and two example configurations are shown in FIGS. 3A and 3B. In some instances, biocompatible fibers are shape memory alloy fibers. Example biocompatible shape memory alloys are discussed below.

Each layer of the annulus fibrosus portions includes a ground matrix. The biocompatible fibers are dispersed in the ground matrix. Generally, the ground matrix includes biocompatible material. As an example, the ground matrix includes biocompatible polymer. Example biocompatible polymers include ethylene-co-vinylacetate, and poly(etherurethanes).

Meshes are vertically disposed between the layers in the example annulus fibrosus portions. Typically, the meshes include a plurality of wires that are connected or closely adjacent to another. Various vertical cross-sectional shapes of the meshes are possible, such as a hexagonal arrangement, a rhomboidal arrangement, a rectangular arrangement, and a triangular arrangement, to name a few.

Materials for the meshes are typically selected such that, at core body temperature (e.g., at 37° C.), the mesh applies almost constant stress even after deformation caused by bulging of the nucleus pulposus portion during loading. Wires in the meshes can be the same materials as those used for the biocompatible fibers, such as shape memory alloy wires.

Exemplary shape memory alloy meshes have austenite finish temperatures less than a core body temperature such that the meshes display pseudoelastic behavior. For example, shape memory alloys used in the meshes can have an austenite finish temperature of less than 37° C. In some instances, shape memory alloys used in the meshes can have an austenite finish temperature of less than 36° C.; less than 35° C.; or less than 30° C.

Fibers within a given layer have the same, or nearly the same, orientation. Orientation can be determined relative to a vertical central axis of the artificial intervertebral disc. Fibers in horizontally-adjacent layers have different orientations, which can result in a crisscross arrangement. For example, fibers in adjacent layers can be 10- to 90-degree rotations of each other. In various embodiments, fibers in adjacent layers are 10-degree rotations; 20-degree rotations; 30-degree rotations; 40-degree rotations; 50-degree rotations; 60-degree rotations; 70-degree rotations; 80-degree rotations; or 90-degree rotations of each other.

In some embodiments, fiber orientation of a given layer is the same as the fiber orientation in a layer once removed. For example, a first layer from the nucleus pulposus and a third layer from the nucleus pulposus each have the same fiber orientation; or a second layer from the nucleus pulposus and a fourth layer from the nucleus pulposus each have the same fiber orientation.

Annulus pulposus portions can have different numbers of layers in various implementations. For example, an annulus pulposus portion includes at least two layers; at least three layers; at least four layers; at least five layers; at least six layers; at least seven layers; at least eight layers; at least ten layers; at least twelve layers; or at least fourteen layers. In various embodiments, annulus pulposus portions include 2 layers; 3 layers; 4 layers; 5 layers; 6 layers; 7 layers; 8 layers; 9 layers; 10 layers; 11 layers; 12 layers; 13 layers; 14 layers; or 16 layers.

In some instances, each layer in the annulus pulposus portion has the same stiffness. In some instances, stiffness of layers in the annulus pulposus portion can be varied. For example, each layer horizontally further from the nucleus pulposus portion has greater stiffness than the adjacent layer closer to the nucleus pulposus portion. As another example, stiffness changes every second layer from the nucleus pulposus portion. That is, for example, the first and second layers have a first stiffness and the third and fourth layers have a second stiffness that is greater than the first stiffness. In these implementations, fiber layers closer to the nucleus pulposus have lesser stiffness than the outer layers of the annulus fibrosus.

Stiffness between layers can be varied in different ways. For example, stiffness can be selected using wire thickness—layers with greater stiffness have thicker wires than layers with lesser stiffness. As another example, stiffness can be selected by varying the number of wires in fibers that are within a given layer. As another example, stiffness can be selected by using different wire materials having different stiffness properties.

C. Example Plates

Example artificial intervertebral discs disclosed and contemplated herein typically include one or more horizontal plates. A plate can be positioned adjacent top and bottom surfaces of the artificial intervertebral disc, termed a top plate and a bottom plate, respectively.

Generally, the example plates provide a platform for the attachment of the layers, including the biocompatible fibers and the shape memory alloy meshes. For example, a top portion of each of the layers is connected to a top plate and a bottom portion of each of the layers is connected to a bottom plate. A first end portion of the shape memory alloy meshes can connect to the top plate and a second, opposite end portion can connect to the bottom plate. Similarly, a first end of the biocompatible fibers can be connected to the top plate and a second end of the biocompatible fibers can be connected to the bottom plate.

Additionally, the plates can facilitate connection of the example artificial intervertebral discs to neighboring vertebrae. In some embodiments, the plates are planar. In other embodiments, the plates are non-planar and can include curved portions.

Various materials can be used for the plates. As an example, cobalt chromium molybdenum alloy (CoCrMo alloy) can be used in construction of the plates. As another example, titanium (Ti) can be used in construction of the plates. In some embodiments, the plates can have a porous coating to promote ingrowth of bone (e.g., vertebral bone) that the plates are attached to.

D. Example Shape Memory Alloys

Shape memory alloys are used with various components of example artificial intervertebral discs disclosed and contemplated herein. Example biocompatible shape memory alloys have an austenite finish temperature less than the body core temperature. Typical body core temperature is about 37° C. In some embodiments, shape memory alloys used in example artificial intervertebral discs have an austenite finish temperature of less than 37° C. In some embodiments, shape memory alloys used in example artificial intervertebral discs have an austenite finish temperature of less than 36° C.; less than 35° C.; or less than 30° C.

Various materials can be used as biocompatible shape memory alloys. Example biocompatible shape memory alloys include alloys based on nickel-titanium (Ni—Ti) such as Nitinol, and alloys based on copper (Cu), such as Cu—Zn—Al and Cu—Al—Ni.

II. Example Embodiments of Artificial Intervertebral Discs

Example embodiments of artificial intervertebral discs are described below with reference to FIGS. 1-5.

FIG. 1 is a schematic, top view of example artificial intervertebral disc 100. Artificial intervertebral disc 100 includes nucleus pulposus portion 102 and annulus fibrosus portion 104. Annulus fibrosus portion 104 includes layers 106 and shape memory alloy mesh 108 but not nucleus pulposus portion 102. As shown, artificial intervertebral disc 100 includes four layers 106, although, as discussed elsewhere within this disclosure, more or fewer layers 106 are contemplated. FIG. 2 is a side view of FIG. 1 along line A and is discussed concurrently with FIG. 1. FIGS. 1 and 2 do not show a top plate or a bottom plate. Other embodiments can include more or fewer components.

Artificial intervertebral disc 100 can have various cross-sectional shapes. In some instances, the cross-sectional shape of artificial intervertebral disc 100 is circular or oval shaped. Nucleus pulposus portion 102 is disposed in a horizontally off-center position within artificial intervertebral disc 100.

Layers 106 are arranged annularly about the nucleus pulposus portion 102. Each layer 106 includes biocompatible fibers 110. As shown, a thickness T (i.e., measured horizontally) of each layer 106 can vary at different locations within artificial intervertebral disc 100. Further, each layer 106 can have a different thickness than adjacent layers 106 at a similar relative location in artificial intervertebral disc 100.

Shape memory alloy mesh 108 is disposed between adjacent layers 106 in artificial intervertebral disc 100. Shape memory alloy mesh 108 also surrounds nucleus pulposus portion 102. Shape memory alloy mesh 108 is configured to provide almost constant stress even after deformation that is caused by bulging of nucleus pulposus portion 102 during loading. Example characteristics of shape memory alloy mesh 108, such as austenite finish temperature, are described in greater detail above. Example embodiments of shape memory alloy mesh 108 are shown in, and described in greater detail below with reference to, FIGS. 3A and 3B.

Biocompatible fibers 110 in annulus fibrosus portion 104 are arranged in a generally crisscross fashion. An example configuration of a crisscross arrangement is most clearly shown in FIG. 2. Example crisscross arrangements can be provided when biocompatible fibers 110 in a given layer 106 are oriented to be rotations of biocompatible fibers 110 in an adjacent layer 106.

Fibers in adjacent layers are rotations of each other, labeled as angle θ. Angle θ is the angle formed by the "intersection" of wires in adjacent layers. Angle θ, in various implementations, may be acute, right, or obtuse. It will be appreciated that the wires do not actually intersect between layers. Angle θ is approximately 84° in FIG. 2, although, as mentioned above, fibers in adjacent layers can have different relative orientations.

FIGS. 3A and 3B are schematic, vertical cross-sectional views of exemplary shape memory alloy meshes 208 and 308, respectively. Shape memory alloy mesh 208 includes shape memory alloy wires 212 in a rhomboidal arrangement. As shown in FIG. 3A, shape memory alloy mesh 208 includes nine shape memory alloy wires 212, although other embodiments can include more or fewer shape memory alloy wires 212.

Shape memory alloy mesh 308 includes shape memory alloy wires 312 in a hexagonal arrangement. As shown in FIG. 3B, shape memory alloy mesh 308 includes nine shape memory alloy wires 312. Other embodiments of shape memory alloy mesh 308 can include more or fewer shape memory alloy wires 312.

Figure 4:
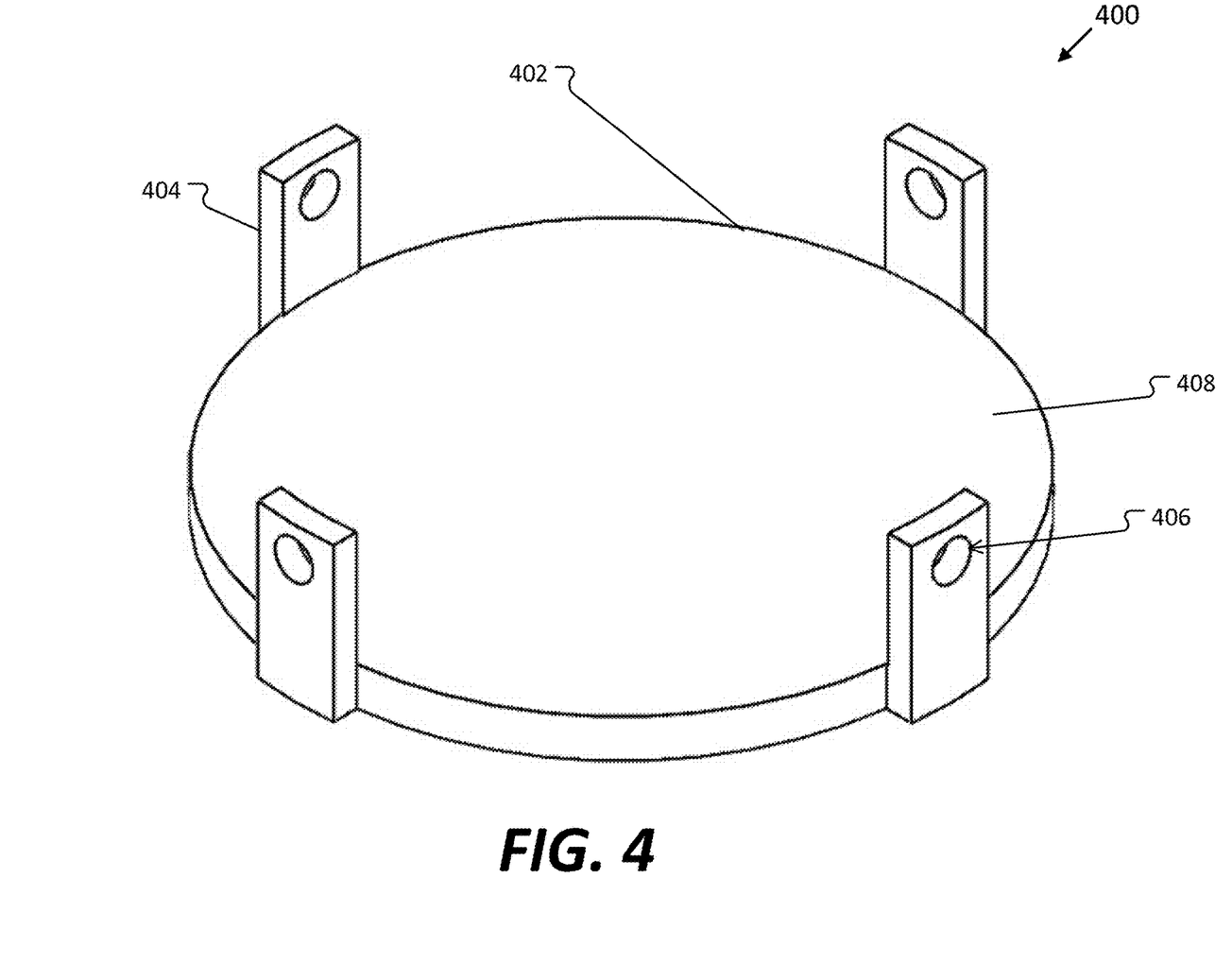
FIG. 4 is a top perspective view of an example plate usable with the artificial intervertebral disc shown in FIG. 1.

FIG. 4 shows example plate 400 that can be used with example artificial intervertebral disc 100. In a typical implementation, artificial intervertebral disc 100 includes two plates 400 such that one plate connects to a vertebra and the opposite plate connects to a different vertebra (e.g., a lower and an upper vertebra relative to the disc).

Plate 400 includes disc 402 and a plurality of tabs 404. In the embodiment shown, plate 400 includes four tabs 404 spaced circumferentially about disc 402. In other embodiments, plate 400 can include more or fewer tabs, such as three tabs 404, five tabs 404, and six tabs 404. In some instances, tabs 404 are arranged symmetrically about disc 402.

In some instances, each tab 404 defines aperture 406. Each aperture 406 can be configured to facilitate securing plate 400 to a vertebra. In some instances, aperture 406 is threaded.

In an example implementation, top surface 408 of disc 402 contacts an adjacent vertebra, and a bottom surface of disc 402 (not visible in FIG. 4) contacts artificial intervertebral disc 100. Screws, not shown in FIG. 4, can then pass through apertures 406 and secure to the adjacent vertebra. In implementations with plate 400 as the top and bottom plate, artificial intervertebral disc 100 attaches via eight screws: four screws through four tabs 404 on the top plate 400 and four screws through four tabs 404 on the bottom plate 400.

Figure 5:
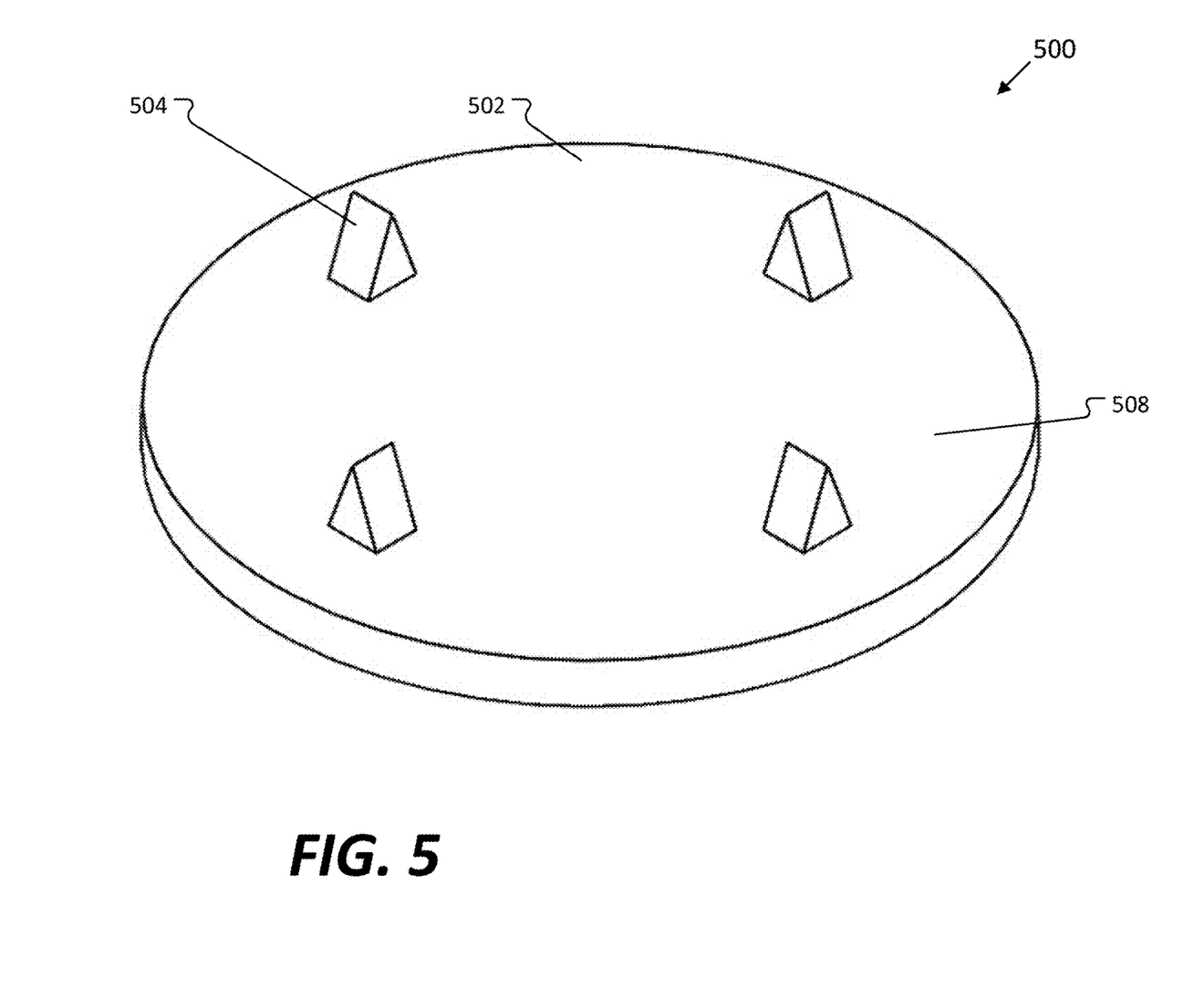
FIG. 5 is a top perspective view of another example plate usable with the artificial intervertebral disc shown in FIG. 1.

FIG. 5 shows another embodiment of plate 500. Similar to plate 400, plate 500 is configured to be positioned between artificial intervertebral disc 100 and adjacent vertebrae. Plate 500 includes a plurality of spikes 504 extending from top surface 508 of plate 500. Spikes 504 are sized and configured to anchor plate 500 to adjacent vertebrae. As shown, plate 500 includes four spikes 504, although other embodiments can include more or fewer spikes 504.

In some embodiments, a top and/or a bottom plate can include both tabs and spikes. Various numbers of spikes and tabs can be combined. For example, and without limitation, a plate can include four tabs and four spikes; six tabs and two spikes; six tabs and four spikes, etc.

III. Example Methods for Attaching Artificial Intervertebral Discs

Artificial intervertebral discs disclosed and contemplated herein can be attached to human vertebrae. In some embodiments, the top plates and bottom plates of artificial intervertebral discs are porous to allow fusion of the plates to the vertebral bone. In some embodiments, the top plates and bottom plates of artificial intervertebral discs have a roughness to facilitate attachment to the vertebral bones.

In some embodiments, an artificial intervertebral disc is secured to a vertebra by passing screws through disc tabs and into the upper and lower vertebrae. In some embodiments, an artificial intervertebral disc is secured to a vertebra using spikes on a disc, which can anchor the disc to the upper and lower vertebral bodies.

IV. Example Methods for Assembling Exemplary Artificial Intervertebral Discs

Figure 6:
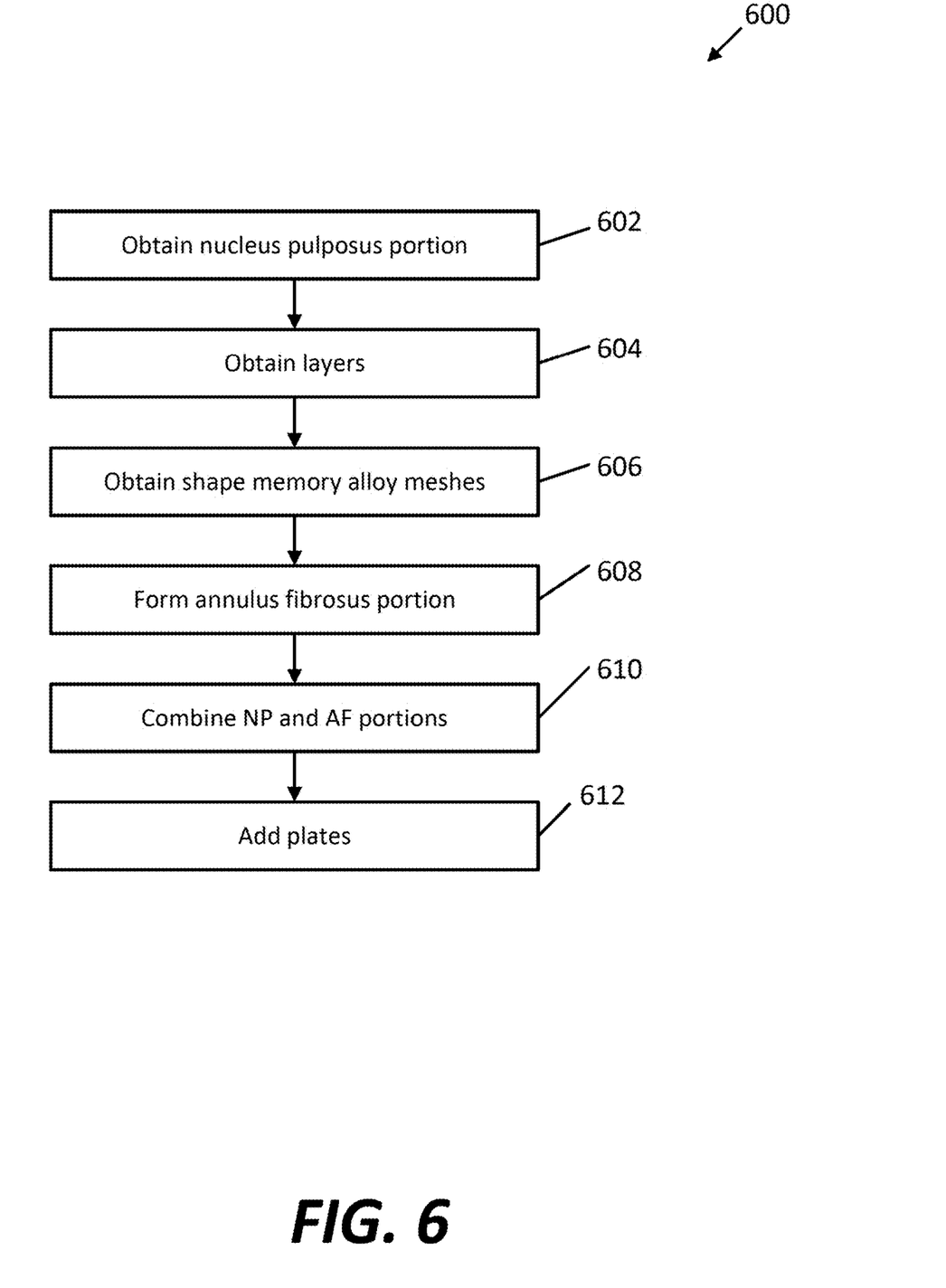
FIG. 6 shows an example method for assembling an exemplary artificial intervertebral disc.

FIG. 6 shows an example method 600 for assembling an example artificial intervertebral disc. Method 600 can be performed to assemble, for instance, exemplary artificial discs described above and shown in FIGS. 1-5. Other embodiments can include more or fewer operations.

Method 600 begins by obtaining a nucleus pulposus (NP) portion (operation 602), a number of layers (operation 604), and shape memory alloy (SMA) meshes (operation 606). The NP portion obtained during operation 602 can include one or more aspects of exemplary NP portions described above.

Obtaining the number of layers (operation 604) can include considering the dimensions that are appropriate to wrap around the NP portion and the neighboring layers. Obtaining the number of layers (operation 604) can include considering the location of the NP portion that may or may not be at the geometric center of the artificial intervertebral disc.

The shape memory alloy meshes are obtained (operation 606) to wrap around the layers including the layer that wraps around the NP portion. The SMA meshes can include one or more aspects of the SMA meshes described above.

Next, the annulus fibrosus portion is formed (operation 608). During operation 608, the layers can be molded individually before assembly to include the SMA fibers using molding processes such as casting, injection molding, or any other process that can accomplish the same functionality. The combination of the layers and SMA meshes, taken together, can form the annulus fibrosus (AF) portion of the artificial intervertebral disc.

Next, the NP portion can be inserted into an SMA mesh and then the NP/SMA mesh can be inserted into a layer (operation 610). This operation continues until all layers and SMA meshes are consumed. Between the layers where the meshes are sandwiched, a bonding process can be used to bind the layers and meshes. Example bonding processes can include a biocompatible medical adhesive such as an epoxy or silicone.

As an alternative, the AF portion can be formed first by placing the SMA meshes and fibers in certain intervals and creating an empty space inside the AF portion. Typically, this can be done when each layer has the same material properties. Then the NP portion can be bonded to the empty space inside the AF portion using a bonding process such as biocompatible medical adhesives.

Next, plates can be added (operation 612), where the plates include one or more attributes of plates shown in, and described above with reference to, FIG. 4 and FIG. 5. The plates can be bonded to the AF/NP structure using a medical adhesive or an alternative method. An alternative method can include bonding the plates to the top and bottom surfaces of a cage that encloses the AF/NP structure and is itself bonded to the structure. Such a construction can enhance the structure's integrity under loading of the spine. The outermost layer of the AF can include another SMA mesh for structural integrity, despite the fact that the layer is already bonded to the neighboring layer and SMA mesh with a process such as biocompatible medical adhesives.

In an alternative to method 600, in certain instances where all layers have the same material properties, an assembly method can begin by creating a subassembly using SMA meshes, fibers (which can be oriented as described above) and plates (such as those shown in FIG. 4 and FIG. 5). In such alternative methods, a skeleton of the disc can be formed by attaching SMA meshes and fibers to the plates after a NP portion is secured between the plates using a bonding process such as biocompatible medical adhesive. Then, the layers can be consecutively formed by using a molding process such as injection molding.

For the recitation of numeric ranges herein, each intervening number therebetween with the same degree of precision is contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are contemplated.

It is understood that the foregoing detailed description and accompanying examples are merely illustrative and are not to be taken as limitations upon the scope of the disclosure. Various changes and modifications to the disclosed embodiments will be apparent to those skilled in the art. Such changes and modifications, including without limitation those relating to the chemical structures, substituents, compositions, or methods of use, may be made without departing from the spirit and scope of the disclosure.

What is claimed is:

1. An intervertebral disc, comprising:
a nucleus pulposus portion including a flexible sealed enclosure, the flexible sealed enclosure including filling material therein;
an annulus fibrosus portion including a plurality of layers arranged annularly about the nucleus pulposus portion, wherein each of the plurality of layers includes biocompatible fibers; and
wherein a first layer fiber orientation of a first fiber layer is different from a second layer fiber orientation of a second fiber layer, the second fiber layer being adjacent to the first fiber layer; and
a shape memory alloy mesh disposed between adjacent layers in the annulus fibrosus portion, the shape memory alloy mesh having an austenite finish temperature of less than 37° C.

2. The intervertebral disc according to claim 1, the shape memory alloy mesh including a plurality of shape memory alloy wire portions provided in a hexagonal arrangement.

3. The intervertebral disc according to claim 1, the shape memory alloy mesh including a plurality of shape memory alloy wire portions provided in a rhomboidal arrangement.

4. The intervertebral disc according to claim 1, the austenite finish temperature being less than 30° C.

5. The intervertebral disc according to claim 1, the plurality of layers including at least four layers of biocompatible fibers, each of the at least four layers of biocompatible fibers being separated by a plurality of shape memory alloy meshes.

6. The intervertebral disc according to claim 5, the plurality of layers including at least eight layers of biocompatible fibers, each of the at least eight layers of biocompatible fibers being separated by a plurality of shape memory alloy meshes.

7. The intervertebral disc according to claim 1, the filling material being an incompressible fluid.

8. The intervertebral disc according to claim 7, the incompressible fluid being a gel.

9. The intervertebral disc according to claim 1, the biocompatible fibers being shape memory alloy fibers.

10. The intervertebral disc according to claim 1, further comprising a top plate and a bottom plate, wherein at least a top portion of each of the plurality of layers is connected to the top plate and at least a bottom portion of each of the plurality of layers is connected to the bottom plate.

11. The intervertebral disc according to claim 10, wherein a first end portion of the plurality of shape memory alloy meshes connects to the top plate and wherein a second end portion of the plurality of shape memory alloy meshes connects to the bottom plate.

12. The intervertebral disc according to claim 11, wherein a first end of the biocompatible fibers are connected to the top plate and a second end of the biocompatible fibers are connected to the bottom plate.

13. The intervertebral disc according to claim 1, wherein the first fiber layer has a first stiffness and wherein the second fiber layer has a second stiffness; and wherein the first stiffness is not equal to the second stiffness.

14. The intervertebral disc according to claim 13, wherein the first stiffness is less than the second stiffness; and
    wherein the first fiber layer surrounds an annular portion of the flexible sealed enclosure; and
    wherein the second fiber layer surrounds the first fiber layer.

15. The intervertebral disc according to claim 1, wherein the first layer fiber orientation is a 30 degree rotation of the second layer fiber orientation.

16. The intervertebral disc according to claim 1, wherein the first layer fiber orientation is a 40 degree rotation of the second layer fiber orientation.

17. The intervertebral disc according to claim 1, the filling material being a silicone rubber material.

18. An intervertebral disc, comprising:
    a nucleus pulposus portion including a flexible sealed enclosure, the flexible sealed enclosure including filling material therein, and the nucleus pulposus portion having an off-center position in the intervertebral disc; and
    an annulus fibrosus portion including a plurality of layers arranged annularly about the nucleus pulposus portion,
        wherein each of the plurality of layers includes biocompatible fibers; and
        wherein a first layer fiber orientation of a first fiber layer is different from a second layer fiber orientation of a second fiber layer, the second fiber layer being adjacent to the first fiber layer.

19. A method for assembling an artificial intervertebral disc, the method comprising:
    obtaining a nucleus pulposus portion including a flexible sealed enclosure, the flexible sealed enclosure including filling material therein;
    obtaining a plurality of layers;
    obtaining shape memory alloy meshes having an austenite finish temperature of less than 37° C.;
    forming an annulus fibrosus portion using the plurality of layers and the shape memory alloy meshes, the annulus fibrosus portion including a plurality of layers arranged annularly about the nucleus pulposus portion,
        wherein each of the plurality of layers includes biocompatible fibers;
        wherein a first layer fiber orientation of a first fiber layer is different from a second layer fiber orientation of a second fiber layer, the second fiber layer being adjacent to the first fiber layer; and
        wherein the shape memory alloy meshes are disposed between adjacent layers in the annulus fibrosus portion;
    combining the nucleus pulposus portion and the annulus fibrosus portion to form a combined structure; and
    adding at least one plate to a top surface or a bottom surface of the combined structure.

* * * * *